United States Patent
Kondo et al.

(10) Patent No.: US 10,365,227 B2
(45) Date of Patent: Jul. 30, 2019

(54) DETECTION DEVICE AND DETECTION METHOD

(71) Applicants: SHIN-ETSU HANDOTAI CO., LTD., Chiyoda-ku, Tokyo (JP); RAYRESEARCH CORPORATION, Gunma (JP)

(72) Inventors: Tadao Kondo, Fukushima (JP); Hisato Nakamura, Gunma (JP)

(73) Assignees: SHIN-ETSU HANDOTAI CO., LTD., Chiyoda-ku, Tokyo (JP); RAYRESEARCH CORPORATION, Gunma (JP)

( * ) Notice: Subject to any disclaimer, the term of this patent is extended or adjusted under 35 U.S.C. 154(b) by 0 days.

(21) Appl. No.: 16/084,107

(22) PCT Filed: Feb. 20, 2017

(86) PCT No.: PCT/JP2017/006111
§ 371 (c)(1),
(2) Date: Sep. 11, 2018

(87) PCT Pub. No.: WO2017/163697
PCT Pub. Date: Sep. 28, 2017

(65) Prior Publication Data
US 2019/0041340 A1    Feb. 7, 2019

(30) Foreign Application Priority Data
Mar. 23, 2016    (JP) ................... 2016-058287

(51) Int. Cl.
*G01N 21/00* (2006.01)
*G01N 21/88* (2006.01)
(Continued)

(52) U.S. Cl.
CPC ..... *G01N 21/8806* (2013.01); *G01N 21/9501* (2013.01); *G01N 21/956* (2013.01); *G01N 2201/06113* (2013.01)

(58) Field of Classification Search
CPC . G01B 11/24; H04N 9/07; H04N 9/31; H04N 5/225; G01C 9/02; G03B 21/28;
(Continued)

(56) References Cited

U.S. PATENT DOCUMENTS

2002/0125449 A1* 9/2002 Ishiguro ................ G01N 21/88
250/559.45
2004/0089059 A1 5/2004 Watanabe et al.

FOREIGN PATENT DOCUMENTS

JP    2-4261 A    2/1990
JP    2-247964 A    10/1990
(Continued)

OTHER PUBLICATIONS

Decision to Grant issued in Japanese Patent Application No. 2016-058287 dated Aug. 20, 2018.
(Continued)

*Primary Examiner* — Abdullahi Nur
(74) *Attorney, Agent, or Firm* — Arent Fox LLP (57) ABSTRACT

A detection device 1 includes an irradiator 3, a photodiode 4, and an evaluation portion 5. The irradiator 3 emits laser light to a surface of a substrate W. The light resulting from the laser light reflected at the surface of the substrate W is incident on the photodiode 4, and the photodiode 4 detects a first position P1 at which the light is incident. The evaluation portion 5 includes a calculation portion and a detection portion. The calculation portion calculates an inclination of the surface of the substrate W on the basis of the first position P1 and a second position P2 at which light is incident on the photodiode 4 when the laser light is
(Continued)

reflected at the surface of the substrate W that is flat. The detection portion detects a defect formed on the surface of the substrate W on the basis of the inclination.

13 Claims, 5 Drawing Sheets

(51) Int. Cl.
    *G01N 21/956*     (2006.01)
    *G01N 21/95*     (2006.01)

(58) Field of Classification Search
    CPC .......... G02B 5/20; G01N 21/88; G01N 21/95; G01N 21/892
    See application file for complete search history.

(56) References Cited

FOREIGN PATENT DOCUMENTS

| | | |
|---|---|---|
| JP | 3-97364 A | 4/1991 |
| JP | 4-42945 A | 2/1992 |
| JP | 4-76407 A | 3/1992 |
| JP | 5-326638 A | 12/1993 |
| JP | 6-10656 B2 | 2/1994 |
| JP | 6-60404A A | 3/1994 |
| JP | 8-201305 A | 8/1996 |
| JP | 2001-345357 A | 12/2001 |
| JP | 2003-202284 A | 7/2003 |
| JP | 2004-45064 A | 2/2004 |
| JP | 2013-61233 A | 4/2013 |
| JP | 2014-157854 A | 8/2014 |

OTHER PUBLICATIONS

International Search Report issued in PCT/JP2017/006111 dated Mar. 21, 2017.
International Search Report issued in PCT/JP2017/005111 dated Mar. 21, 2017.
Notification of Reasons for Refusal issued in Japanese Patent Application No. 2016-058287 dated Aug. 20, 2018.
Decision of Refusal dated Mar. 13, 2019, from the Japanese Patent Office in counterpart application No. 2016-058287.

\* cited by examiner

FIG.1

FIG.2A r Direction

FIG.2B r Direction

| | Region of substrate | | | | | | |
|---|---|---|---|---|---|---|---|
| | 3 | 6 | 7,8 | 10 | 11 | 13 | 15 |
| Detection result of comparative example 1 | ○ | × | ○ | × | ○ | × | × |
| Detection result of comparative example 2 | × | × | ○ | × | × | × | × |
| Detection result of comparative example 3 | × | × | ○ | × | × | × | × |
| Total of detection results of comparative examples | 1/3 | 0/3 | 3/3 | 0/3 | 1/3 | 0/3 | 0/3 |
| Detection result of example | ○ | ○ | ○ | ○ | ○ | ○ | ○ |
| Captured image of substrate | | | | | | | |

DETECTION DEVICE AND DETECTION METHOD

CROSS-REFERENCE TO RELATED APPLICATIONS

This present application is a National Stage entry of International Application No. PCT/JP2017/006111, filed Feb. 20, 2017, which claims priority to Japanese Patent Application No. 2016-058287, filed Mar. 23, 2016. The disclosures of the prior applications are incorporated in their entirety reference herein.

FIELD OF THE INVENTION

The invention relates to a detection device and a detection method.

BACKGROUND OF THE INVENTION

With the recent increases in the level of integration density of semiconductor devices, it is becoming very important to deal with crystal defects of a semiconductor single crystal substrate (hereinafter referred to as a semiconductor substrate or also simply a substrate), from which a semiconductor device is formed, in particular, crystal defects formed in the vicinity of the surface of the single crystal substrate. If a semiconductor single crystal substrate on which any crystal defect is formed is used to produce a semiconductor device, the quality of the produced semiconductor device will be significantly affected. Therefore, in order to improve the quality of such a semiconductor device, it is necessary to evaluate crystal defects in the vicinity of the surface of a semiconductor single crystal substrate serving as the substrate of the semiconductor device, and to know the status thereof.

As an evaluation method for the semiconductor substrate, for example, a visual inspection has been conventionally performed in which the shape of distribution of crystal defects appearing on the surface of a semiconductor substrate is sketched under a light-condensing lamp to determine the length and the like of the crystal defects, then the measured results are accumulated, and the level of occurrence of the crystal defects is evaluated. As an evaluation method using a measurement device, an X-ray topography method or the like has been carried out in which X-rays are emitted to the substrate, and the X-ray diffraction intensity attributed to the crystal defects formed on the substrate is detected.

For example, in the case of using the above-described visual inspection to quantify the amount of slip dislocations formed on a semiconductor substrate, the slip dislocations observed visually are sketched, and the accumulated length of the slip dislocations will be further determined from the sketch. Therefore, significant time and labor is required. In addition, the test results vary because the measurement is based on human visual perception, and therefore the test needs to be performed by an experienced and skillful person.

In the case of using the above-described X-ray topography method to evaluate the crystal defects, defects that have occurred on the surface as well as the interior and the back surface will be observed. Therefore, it is difficult to evaluate the crystal defects present on the surface of the substrate and the crystal defects present in the interior or the like of the substrate while distinguishing between these defects.

Examples of the other methods using a measurement device include a method using a device that scans the surface of the semiconductor substrate with laser light, and measures the light scattering intensity from particles or the like. With this method, the device mechanically detects crystal defects, so that the variations in the test results can be reduced to a certain degree. However, crystal defects attributed to various crystal defects are contained in the detected crystal defects, and specific crystal defects such as a slip dislocation cannot be selectively quantified.

Patent Document 1 discloses a method in which the scattered light resulting from the laser light emitted to the surface of the semiconductor substrate is detected by a photodiode, and the crystal defects on the semiconductor substrate are evaluated. However, the method of Patent Document 1 is a destructive test that requires the labor of etching the semiconductor substrate in advance, and the accuracy of detection of crystal defects by the photodiode is insufficient.

On the other hand, Patent Documents 2 and 3 disclose methods in which the reflected light resulting from the laser light emitted to the surface of the semiconductor substrate is detected using a photoelectric element to evaluate the slip dislocation.

CITATION LIST

Patent Document

[Patent Document 1] Japanese Laid-Open Patent Publication No. 2001-345357
[Patent Document 2] Japanese Laid-Open Patent Publication No. H8-201305
[Patent Document 3] Japanese Laid-Open Patent Publication No. H4-42945

SUMMARY OF INVENTION

Problems to be Solved by the Invention

The methods disclosed in Patent Documents 2 and 3 are not intended to detect the laser light that changes according to the relationship between the slip dislocation and the crystal orientation to evaluate the slip dislocation of the semiconductor substrate, or to detect the crystal defects formed on the surface of the substrate on the basis of the inclination of the surface of the substrate.

A problem to be solved by the invention is to provide a detection device and a detection method that enable a defect formed on the surface of an object to be detected on the basis of the inclination of the surface of the object.

Solution to the Problems and Effects of the Invention

A detection device according to the invention includes:
an irradiation portion that emits laser light to a surface of an object;
a light-detecting portion on which light resulting from the laser light reflected at the surface is incident, and that detects a first position at which the light is incident;
a calculation portion that calculates an inclination of the surface on the basis of the first position and a second position at which light is incident on the light-detecting portion when the laser light is reflected at the surface that is flat; and
a detection portion that detects a defect formed on the surface on the basis of the inclination calculated by the calculation portion.

The reflection angle at which laser light is reflected at the surface of an object changes according to the inclination of the surface at which the laser light is reflected, and the laser light that has been reflected at the surface is incident on the light-detecting portion. Thus, a displacement between the first position at which the laser light reflected at the surface is incident on the light-detecting portion and the second position at which the laser light reflected at a flat surface when the surface at which the laser light is reflected is flat is incident on the light-detecting portion changes according to the inclination angle of the surface of the object. Accordingly, it is possible to calculate the inclination of the surface of the object on the basis of the first position and the second position. The inventors have found that when a defect occurs on the surface of an object, for example, a minute height difference is created on the surface of the object, resulting in a change in the inclination of the surface of the object that is calculated in the above-described manner. Therefore, with a detection device according to the invention, it is possible to detect a defect formed on the surface of the object on the basis of the calculated inclination.

In an embodiment of the invention, the calculation portion calculates the inclination in a first direction extending in a horizontal direction on the basis of a difference between the first position and the second position in the first direction.

This makes it possible to calculate the inclination of the surface of the object in the first direction.

In an embodiment of the invention, the calculation portion calculates the inclination in a second direction that is orthogonal to the first direction in the horizontal direction on the basis of a difference between the first position and the second position in the second direction.

This makes it possible to calculate the inclination of the surface of the object in the second direction. Note that the surface shape of the object can be calculated from the inclinations of the surface in the first and second directions.

In an embodiment of the invention, the detection device includes a moving portion including a support portion that supports the object, and being movable in a horizontal direction and rotatable about an axis extending in a vertical direction, wherein the surface is scanned with the laser light by the moving portion supporting and moving the object, and the calculation portion calculates an inclination of the surface at each point on the basis of the first position of light resulting from the laser light reflected at the point on the surface.

This makes it possible to calculate the inclination of the surface at each point that has been scanned with the laser light.

In an embodiment of the invention, the surface of the object includes a silicon single crystal, the irradiation portion emits the laser light having a wavelength of 405 nm or less to the surface, and the detection portion detects a slip dislocation that is the defect.

This makes it possible to detect a slip dislocation formed on the surface of the object.

In an embodiment of the invention, the light-detecting portion is a quadrant photodiode.

This makes it possible to easily calculate the first position. Also, it is possible to detect a slip dislocation formed on the surface of, for example, a silicon single crystal substrate, without destructing the object.

In an embodiment of the invention, the object is a silicon single crystal substrate, a silicon single crystal substrate including an epitaxial layer (epitaxial wafer), a silicon single crystal ingot block, or an SOI wafer.

This makes it possible to calculate defects formed on the surfaces of various materials associated with a silicon single crystal. As used herein, an SOI wafer means a bonded SOI wafer including an SOI (Silicon On Insulator) layer formed by forming an oxide film on one of two silicon single crystal substrates, bonding the silicon single crystal substrates with the formed oxide film interposed therebetween, and subsequently forming the silicon single crystal substrate on which the device is to be fabricated into a thin film.

A detection method according to the invention includes the steps of:

emitting laser light to a surface of an object;

calculating an inclination of the surface on the basis of a first angle that is a reflection angle of light resulting from the laser light reflected at the surface, and a second angle that is a reflection angle of light when the laser light is reflected at the surface that is flat; and detecting a defect formed on the surface on the basis of the inclination calculated in the calculating step.

The invention is configured as a detection method. As with the above-described detection device, the reflection angle at which laser light is reflected at a surface of an object changes according to the inclination of the surface. Accordingly, a displacement between the first angle of the light reflected at the surface and the second angle of light that is reflected when the surface is flat changes according to the inclination angle of the surface of the object. Thus, it is possible to calculate the inclination of the surface of the object on the basis of the first and second angles, and it is possible to detect a defect formed on the surface of the object on the basis of the calculated inclination of the surface.

In an embodiment of the invention, in the calculating step, the inclination in a first direction extending in a horizontal direction is calculated on the basis of a difference between the first angle and the second angle in the first direction.

This makes it possible to calculate the inclination of the surface of the object in the first direction.

In an embodiment of the invention, in the calculating step, the inclination in a second direction that is orthogonal to the first direction in the horizontal direction is calculated on the basis of a difference between the first angle and the second angle in the second direction.

This makes it possible to calculate the inclination of the surface of the object in the second direction. Note that the surface shape of the object can be calculated from the inclinations of the surface in the first and second directions.

In an embodiment of the invention, the emitting step includes scanning the surface with the laser light by moving the object, and, in the calculating step, an inclination of the surface at each point is calculated on the basis of the first angle of light resulting from the laser light reflected at the point on the surface.

This makes it possible to calculate the inclination of the surface at each point that has been scanned with the laser light.

In an embodiment of the invention, in the emitting step, the laser light having a wavelength of 405 nm or less is emitted to the surface of the object, the surface of which includes a silicon single crystal, and, in the defect detecting step, a slip dislocation that is the defect is detected.

This makes it possible to detect a slip dislocation formed on the surface of the silicon single crystal.

In an embodiment of the invention, a silicon single crystal substrate, a silicon single crystal substrate including an epitaxial layer (epitaxial wafer), a silicon single crystal ingot block, or an SOI wafer is used as the object.

This makes it possible to calculate defects formed on the surfaces of various materials associated with a silicon single crystal.

DESCRIPTION OF EMBODIMENTS

Figure 1:
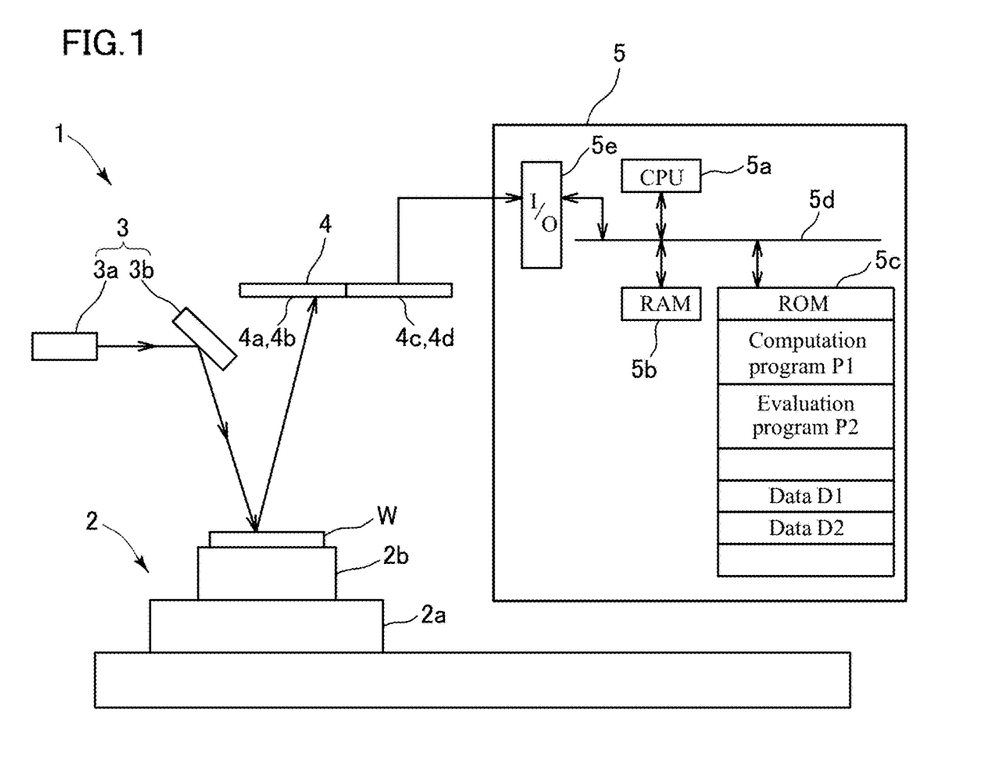
FIG. 1 is a schematic diagram of a detection device as an example according to the invention.

FIG. 1 shows a detection device 1 as an example according to the invention. For example, the detection device 1 calculates an inclination of a surface of a silicon single crystal substrate (hereinafter referred to as "substrate W") to detect a slip dislocation formed on the surface of the substrate W.

The detection device 1 includes a stage 2 that supports and moves the substrate W, an irradiator 3 that emits light to the surface of the substrate W supported by the stage 2, a quadrant photodiode (hereinafter referred to as "photodiode 4") on which the light reflected at the substrate W is incident, and an evaluation portion 5 that evaluates the substrate W on the basis of a result of detection by the photodiode 4.

Figure 2A:
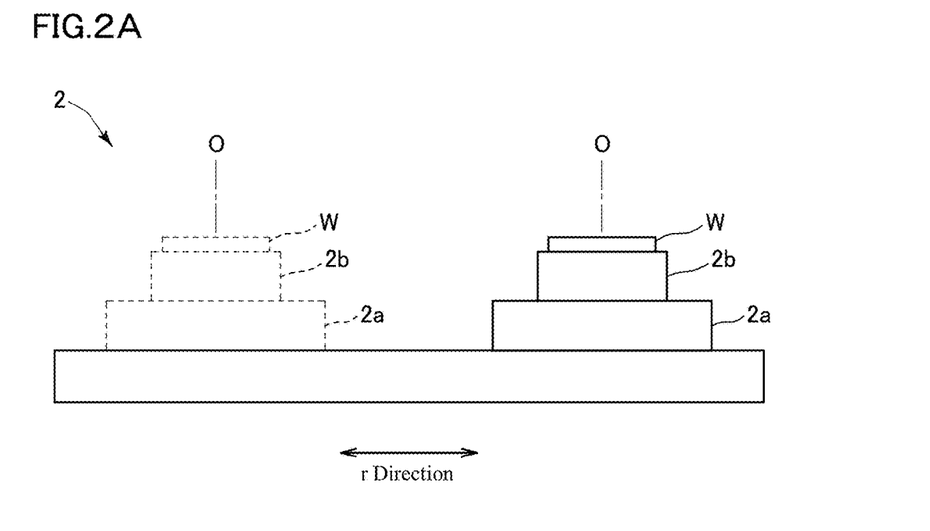
FIG. 2A is a schematic front view showing a stage on which the silicon single crystal substrate shown in FIG. 1 is placed.
Figure 2B:
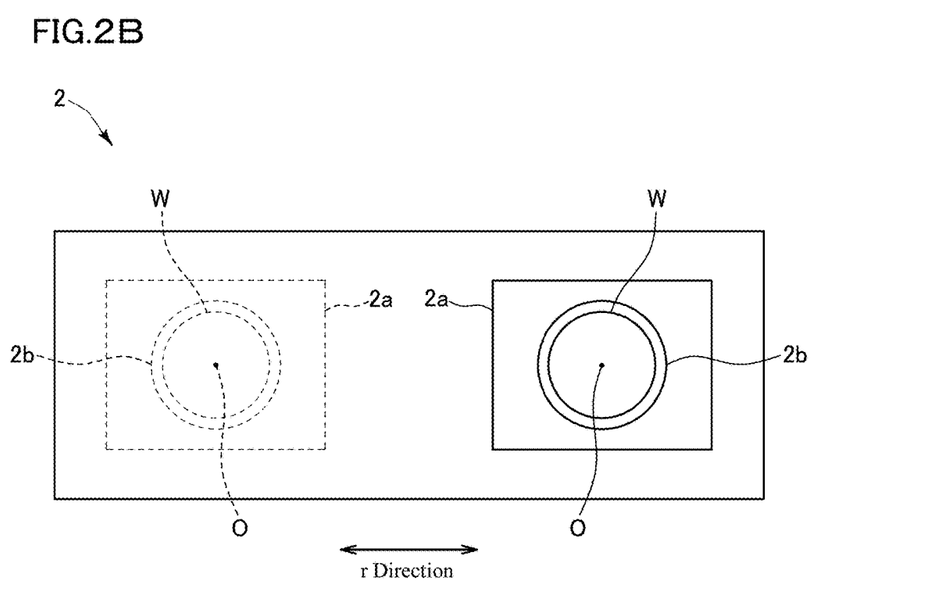
FIG. 2B is a schematic plan view of FIG. 2A.

As shown in FIGS. 2A and 2B, the stage 2 is a so-called rθ stage that is movable in a horizontal direction and is rotatable about an axis O extending in a vertical direction. The stage 2 includes an r stage 2a that is linearly movable in the illustrated r direction, which is the horizontal direction, and a θ stage 2b that is provided on the r stage 2a and is rotatable about the axis O. The θ stage 2b includes a support portion (not shown) that supports the substrate W by clamping the outer circumferential surface of the substrate W without coming into contact with the back surface of the substrate W. The substrate W supported by the support portion can be rotated about the axis O by the θ stage 2b, and can be moved in the r direction shown in the drawing by the r stage 2a.

Referring back to FIG. 1, light is emitted by the irradiator 3 to the substrate W supported by the stage 2. The irradiator 3 includes a semiconductor laser 3a that emits laser light toward the surface of the substrate W, and a mirror portion 3b that guides the laser light emitted from the semiconductor laser 3a to the surface of the substrate W supported by the stage 2. The semiconductor laser 3a emits blue-purple laser light having a wavelength of 405 nm or less (e.g., a wavelength range of 350 to 405 nm). The laser light that is emitted has a center wavelength of 405 nm, for example.

Figure 3:
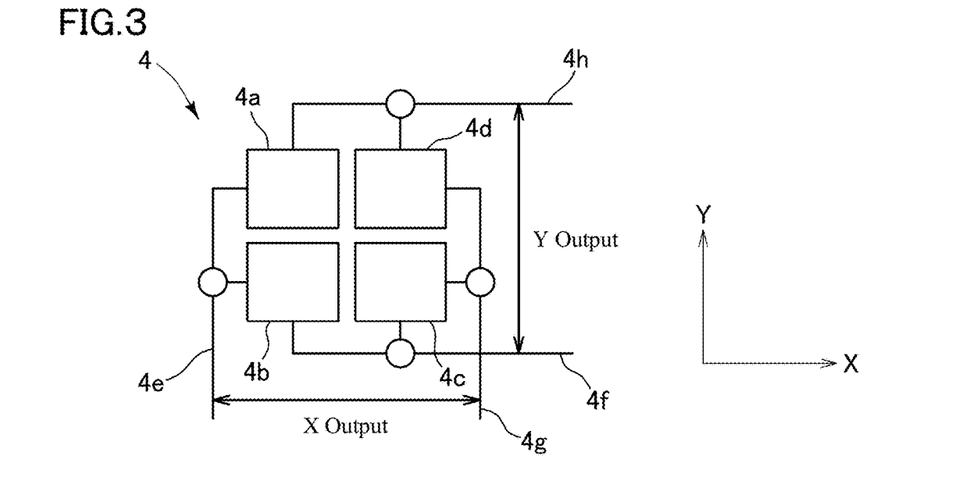
FIG. 3 is a schematic bottom view of the quadrant photodiode shown in FIG. 1.

The laser light emitted to the surface of the substrate W is reflected at the surface of the substrate W, and is subsequently guided to the photodiode 4. FIG. 3 shows a schematic diagram of the photodiode 4 shown in FIG. 1 as viewed from the bottom surface side. The photodiode 4 includes four-part split light-receiving portions 4a to 4d on which the light reflected at the surface of the substrate W is incident, and four output terminals 4e to 4h that output signals according to the position of the light incident on the light-receiving portions 4a to 4d. The light-receiving portions 4a to 4d are elements that convert the light incident on the light-receiving portions 4a to 4d into electric signals. The light-receiving portions 4a to 4d have a square shape as shown in the drawing, and are located on an X-Y plane shown in the drawing extending in the horizontal direction. The light-receiving portions 4a to 4d as a whole are disposed such that a cross-shaped gap having a uniform width is formed at the center. The output terminal 4e outputs signals that are output from the light-receiving portions 4a and 4b according to the incident position of the incident light. The output terminal 4f outputs signals that are output from the light-receiving portions 4b and 4c according to the incident position of the incident light. The output terminal 4g outputs signals that are output from the light-receiving portions 4c and 4d according to the incident position of the incident light. The output terminal 4h outputs signals that are output from the light-receiving portions 4a and 4d according to the incident position of the incident light. Accordingly, for example, the light incident position in the X-axis direction is determined from the difference in output between the output terminal 4e and the output terminal 4g, and the light incident position in the direction of a Y axis that is orthogonal to the X axis is determined from the difference in output between the output terminal 4h and the output terminal 4f. The signals that are output from the output terminals 4e to 4h are transmitted to the evaluation portion 5 as shown in FIG. 1.

The evaluation portion 5 is an entity that evaluates a defect formed on the surface of the substrate W on the basis of the signals transmitted from the photodiode 4. The evaluation portion 5 includes a CPU 5a, a RAM 5b, and a ROM 5c, as well as a bus 5d that connects these components, and an I/O port 5e to which the bus 5d connects. The signals sent from the photodiode 4 are transmitted from the I/O port 5e to the CPU 5a. The CPU 5a executes a program recorded in the ROM 5c to control various types of information processing. For example, the CPU 5a evaluates a defect of the substrate W on the basis of the signals that are output from the photodiode 4. The RAM 5b is a readable and writable memory, and is a volatile storage portion that functions as a work area when the CPU 5a performs information processing. The ROM 5c is a read-only memory. The basic program, parameter, and data for the CPU 5a to operate are recorded in the ROM 5c. A computation program P1 that computes an incident position of the light incident on the photodiode 4, an evaluation program P2 that evaluates a defect of the substrate W on the basis of the incident position, and data D1 and the like used during execution of the evaluation program P2 are stored in the ROM 5c.

The computation program P1 computes the incident position (hereinafter referred to as "first position") of the light incident on the light-receiving portions 4a to 4d, on the basis of the signals from the output terminals 4e to 4h shown in FIG. 3. The computation program P1 computes an incident position of light in the X-axis direction from a difference between the signals that are output from the output terminals 4e and 4g, and computes an incident position of light in the Y-axis direction from a difference between the signals that are output from the output terminals 4f and 4h, thereby calculating the first position.

Referring back to FIG. 1, the evaluation program P2 evaluates a slip dislocation that is a defect formed on the surface of the substrate W by using the first position calculated by the computation program P1 and the data D1 stored in the ROM 5c. The data D1 is data indicating the incident position (hereinafter referred to as "second position") at which reflected light is incident on the light-receiving portions 4a to 4d when the laser light from the semiconductor laser 3a is reflected at a flat portion of the surface of the substrate W. The evaluation program P2 evaluates a slip dislocation formed on the surface of the substrate W on the basis of the first and second positions.

Figure 4:
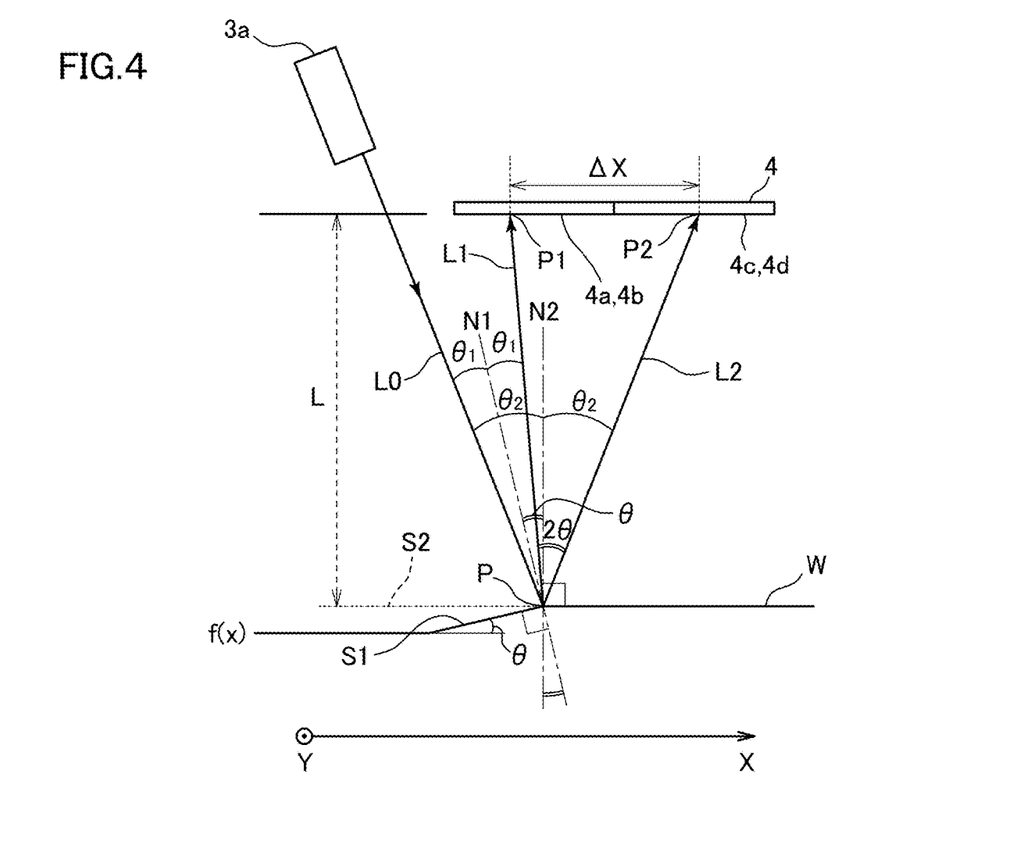
FIG. 4 is a principle diagram illustrating a principle of calculating an inclination of a surface of a silicon single crystal substrate by using the detection device shown in FIG. 1.

Here, FIG. 4 shows how laser light (incident light L0) incident on a point P on the surface of the substrate W that extends in the X-axis direction is reflected to be guided to the photodiode 4. L1 represents reflected light resulting from the incident light L0 reflected at an inclined surface S1, which is the surface of the substrate W inclined at an angle θ relative to the horizontal direction, and L2 represents reflected light resulting from the incident light L0 reflected at a flat surface S2, which is the surface of the substrate W that is flat. The X axis in FIG. 4 corresponds to the X axis in FIG. 3, and FIG. 4 shows an example in which the reflected light L1 in FIG. 4 is incident on the light-receiving portion 4a or 4b, and the reflected light L2 is incident on the light-receiving portion 4c or 4d. The distance in the X-axis direction between an incident position (first position P1) at which the reflected light L1 having been reflected at the inclined surface S1 is incident on the light-receiving portion 4a or 4b and an incident position (second position P2) at which the reflected light L2 having been reflected at the flat surface S2 is incident on the light-receiving portion 4c or 4d is shown as ΔX in FIG. 4. In addition, a distance L between the point P and the light-receiving portion 4a or 4d in the vertical direction is illustrated in FIG. 4. The incident angle and the reflection angle are equal due to the law of reflection. Therefore, when $\theta_1$ is the angle formed between a normal N1 of the inclined surface S1 and the incident light L0, the angle formed between the normal N1 and the reflected light L1 is $\theta_1$. Similarly, when $\theta_2$ is the angle formed between a normal N2 of the flat surface S2 and the incident light L0, the angle formed between the normal N2 and the reflected light L2 is $\theta_2$. Then, the angle formed between the normal N1 and the normal N2 is equal to the inclination angle θ of the inclined surface S1, and is therefore θ. The angle formed between the reflected lights L1 and L2 is $2\theta_2-2\theta_1$, the angle θ formed between the normals N1 and N2 is $\theta_2-\theta_1$. Therefore, the angle formed between the reflected lights L1 and L2 is 2θ. Thus, the distance ΔX in the X-axis direction between the first position P1 at which the reflected light L1 having been reflected at the inclined surface S1 is incident on the light-receiving portion 4a or 4b and the second position P2 at which the reflected light L2 having been reflected at the flat surface S2 is incident on the light-receiving portion 4c or 4d changes according to the angle θ, which is the inclination angle of the inclined surface S1.

Here, assuming that the angle θ at which the inclined surface S1 is inclined is minimum, the distance ΔX can be approximated as: $\Delta X=2\theta \times L$, and the angle θ can be calculated as: $\theta=(\frac{1}{2}L) \times \Delta X$ (hereinafter referred to as "Expression 1"). Thus, a differential value that is a slope of the surface of the substrate W at each point in the X-axis direction can be calculated from Expression 1. By integrating the function of such a differential value, the surface shape (the function f(x) in FIG. 4) of the substrate W in the X-axis direction can be calculated.

Referring back to FIG. 1, the computation program P1 calculates the first position P1 shown in FIG. 4. Meanwhile, the second position P2 is stored as data D1 in the ROM 5c shown in FIG. 1. Thus, the evaluation program P2 calculates the ΔX in FIG. 4 from the calculated first position P1 and the second position P2 in the data D1, and calculates the slope (angle θ) of the inclined surface S1. In this way, the evaluation program P2 calculates the surface shape (function f(x)) of the substrate W in the X-axis direction by calculating the slope (differential value) of the surface of the substrate W at each point in the X-axis direction, and integrating the differential value at each point in the X-axis direction. Similarly, the evaluation program P2 calculates the surface shape of the substrate W in the Y-axis direction that is orthogonal to the X-axis direction, and calculates the overall shape of the surface of the substrate W. Next, the evaluation program P2 detects a slip dislocation formed on the surface of the substrate W from the calculated surface shape. For example, data D2 indicating the surface shape of the substrate W on which a slip dislocation has been formed may be stored in the ROM 5c in FIG. 1, and a slip dislocation formed on the surface of the substrate W may be detected by comparing the surface shape indicated by the data D2 and the calculated surface shape of the substrate W. Note that when the evaluation program P2 detects a slip dislocation, the area of the slip dislocation may be displayed, for example, in a captured image of the surface of the substrate W that has been captured by an imaging device (not shown).

The main portions of the detection device 1 have been described above. Next, a method for evaluating a slip dislocation formed on the surface of the substrate W by placing the substrate W on the stage 2 will be described. When the substrate W has been placed on the stage 2, laser light having a wavelength of 405 nm, for example, is emitted to the surface of substrate W by the semiconductor laser 3a. Then, with the substrate W being supported, the r stage 2a shown in FIG. 2B is moved in the r direction, the θ stage 2b is rotated about the axis O, and the entire surface of the substrate W is scanned with the laser light. As shown in FIG. 4, the reflection angle of the laser light emitted to the surface of the substrate W changes according to the inclination angle (angle θ) of the surface of the substrate W, and the reflected light L1 that has been reflected is incident on the light-receiving portions 4a to 4d. When the reflected light L1 is incident on the light-receiving portions 4a to 4d, signals are transmitted to the evaluation portion 5 in FIG. 1 from the output terminals 4e to 4h in FIG. 3 according to the incident position of the reflected light L1. The evaluation portion 5 calculates, for example, the incident position (first position P1) at which the reflected light L1 shown in FIG. 4 is incident on the light-receiving portions 4a to 4d, from the signals transmitted from the output terminals 4e to 4h. The evaluation portion 5 calculates the distance ΔX between the first position P1 and the second position P2 in the X-axis direction shown in FIG. 4 from the first position P1 and the second position P2 (the data D1 in FIG. 1). Then, the evaluation portion 5 calculates, on the basis of ΔX, a differential value that is a slope (inclination angle θ of the substrate W in the X-axis direction) of the surface of the substrate W at which the incident light L0 has been reflected. Signals indicating the first position P1 at which the light resulting from the laser light reflected at each point on the surface of the substrate W is incident on the light-receiving portions 4a to 4d are sequentially transmitted to the evaluation portion 5, and the evaluation portion 5 obtains a slope (differential value) at each point on the surface of the substrate W from the transmitted signals. Then, the surface shape (function f(x)) of the substrate W in the X-axis direction is calculated by integrating the function of the obtained differential value, and the surface shape of the substrate W in the Y-axis direction is calculated in a similar manner. Thereafter, a slip dislocation formed on the surface of the substrate W is detected from the calculated surface shape.

As described above, in the detection device 1, the inclination of the substrate W can be calculated on the basis of the first position P1 at which the laser light reflected at the surface of the substrate W is incident on the light-receiving portions 4a to 4d and the second position P2 at which the laser light reflected at a flat surface of the substrate W is incident on the light-receiving portions 4a to 4d. Then, the surface shape of the substrate W can be calculated by integrating the function of a slope (differential value) of the surface of the substrate W at each position, and a slip dislocation formed on the surface of the substrate W can be detected from the calculated surface shape. Specifically, the surface shape of the substrate W in the X-axis direction can be calculated on the basis of $\Delta X$, which is the distance between the first position P1 and the second position P2 in the X-axis direction. By calculating the surface shape of the substrate W in the Y-axis direction in a similar manner, the overall shape of the surface of the substrate W can be calculated, and a slip dislocation formed on the surface of the substrate W can be detected from the overall shape of the surface. In the detection device 1, using the photodiode 4 enables the first position P1 in the X-axis direction in FIG. 4 to be easily computed from the difference between the signals that are output from the output terminals 4e and 4g in FIG. 3, and enables the first position P1 in the Y-axis direction to be easily computed from the difference between the signals that are output from the output terminals 4f and 4h in a similar manner.

EXAMPLES

To confirm the effects of the invention, the following experiment was carried out. In the following, the invention will be specifically described by way of an example and comparative examples. However, these examples shall not be construed as limiting the invention.

Example

A silicon single crystal substrate W having a diameter of 300 mm and the detection device 1 were prepared, and the substrate W was placed on the stage 2 of the detection device 1. Next, laser light was emitted to the surface of the substrate W by the semiconductor laser 3a, and the stage 2 was moved to scan the entire surface of the substrate W with the laser light, thereby evaluating slip dislocations of the surface of the substrate W (determining the presence or absence of a slip dislocation).

Comparative Examples

In the comparative examples, using the substrate W used in Example, a slip dislocation appearing on the surface of the substrate W was visually inspected. In the comparative examples, the presence or absence of a slip dislocation appearing on the surface of the substrate W was visually determined by three inspectors (Comparative Examples 1 to 3).

Figure 5:
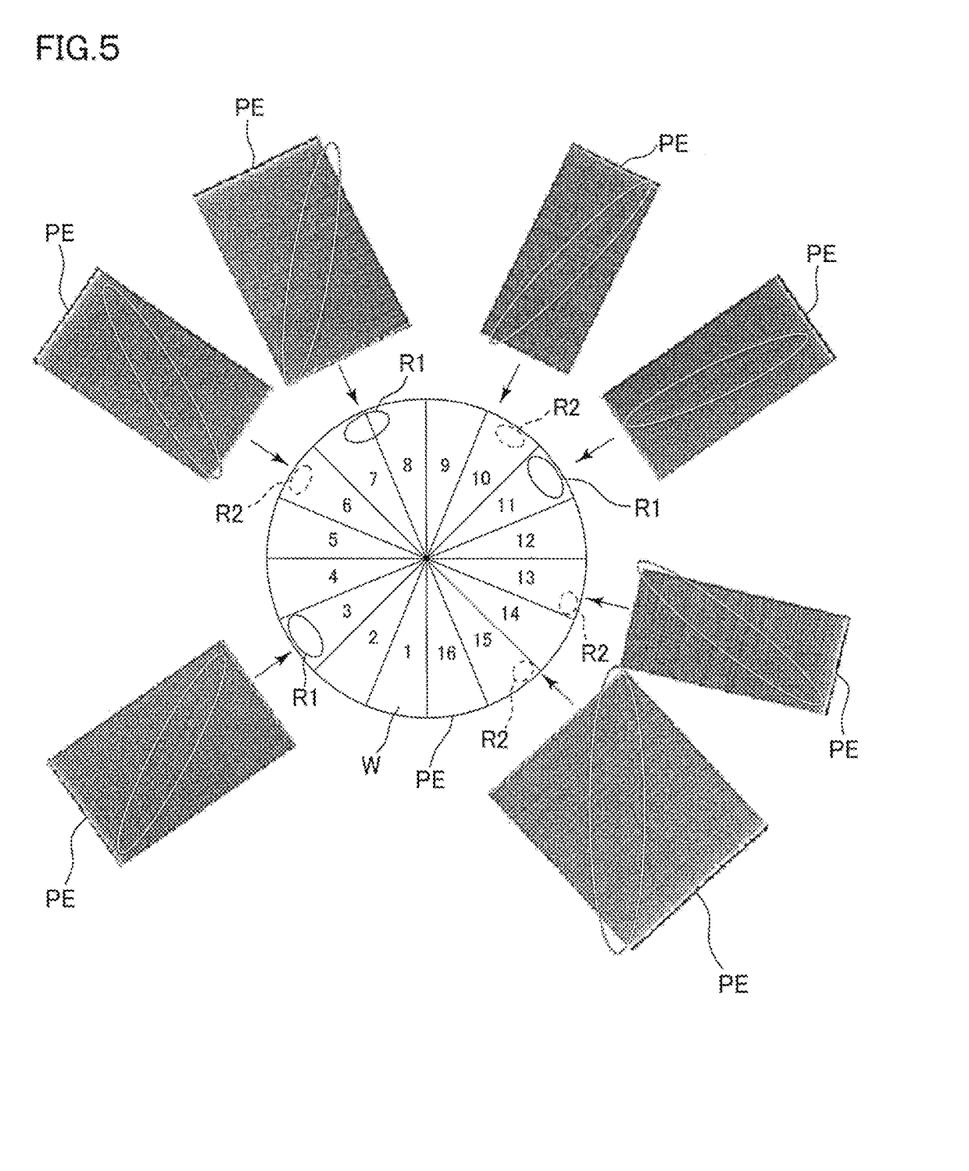
FIG. 5 is a schematic plan view showing images of slip dislocations detected in Example and Comparative Examples 1 to 3, and a substrate showing the positions of the slip dislocations.

FIG. 5 shows a schematic plan view of images of the slip locations detected in Example and Comparative Examples 1 to 3, and the substrate W showing the positions of the detected slip dislocations. The numerals shown in the substrate W represent regions defined by equally dividing the substrate W into 16 portions with the center of the substrate W as a base point. Regions R1 enclosed by the solid line circles shown in the regions 3, 7, 8, and 11 indicate the regions in which a slip dislocation was detected in both Example and Comparative Examples 1 to 3. Regions R2 enclosed by the broken line circles shown in the regions 6, 10, 13, and 15 are the regions in which a slip dislocation was detected only in Example. Note that there was no region in which a slip dislocation was detected only in the comparative examples. In FIG. 5, a side denoted by reference character PE in each rectangular image indicates an outer circumferential portion of the substrate W, and a slip dislocation is shown inside the ellipse indicated in the image.

Figure 6:
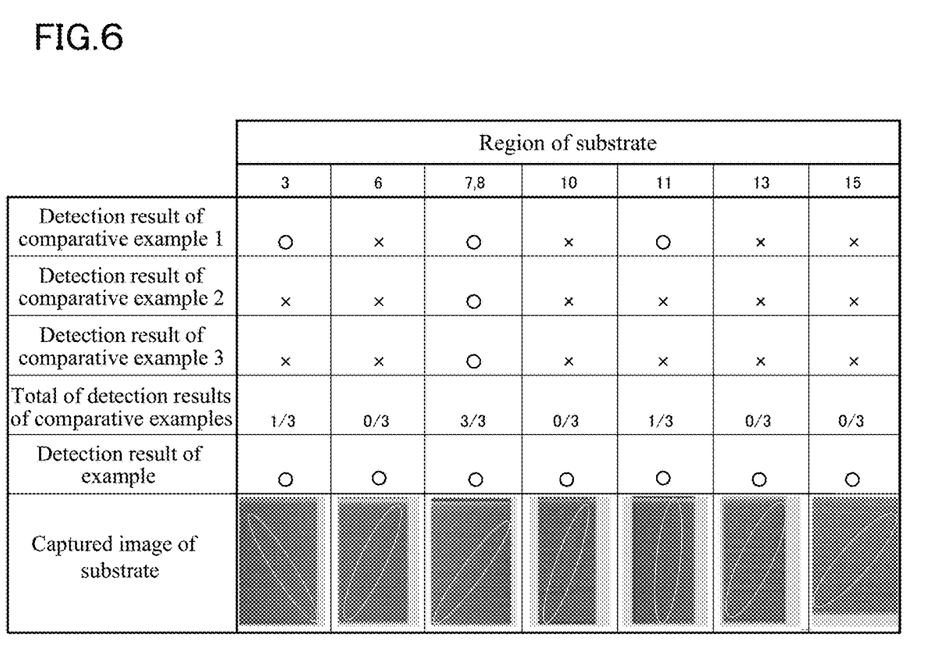
FIG. 6 is a table showing detection results of the slip dislocations detected in Example and Comparative Examples 1 to 3, and images of the slip dislocations formed on the substrate.

FIG. 6 shows results of the detection in which slip dislocations were detected in Example and Comparative Examples 1 to 3. In Comparative Example 1, the slip dislocations formed in the regions 3, 7 (and 8), and 11 in FIG. 5 were detected. In Comparative Examples 2 and 3, only the slip dislocations formed in the region 7 (and 8) in FIG. 5 were detected. Thus, in Comparative Examples 1 to 3, the result of detection of the slip dislocation differed among the inspectors, and as a whole, only the slip dislocations formed in the regions 3, 7 (and 8), and 11 in FIG. 5 were detected. On the other hand, in Example, the slip dislocations formed in the regions 6, 10, 13, and 15, in addition to the regions in which the slip dislocation was detected in Comparative Examples 1 to 3, were detected. Therefore, in Example, the slip dislocations that had not been visually detected were detected in a reliable manner.

Although the examples of the invention have been described above, the invention is not limited to the specific description thereof. The illustrated configurations and the like can be combined as appropriate within a range where there is no technical contradiction to practice the invention, or a certain element or process can be substituted with a known form to practice the invention.

Although the above description shows an example in which the detection device 1 evaluates a slip dislocation formed on the surface of the substrate W, the detection device 1 can also evaluate a slip dislocation formed on a silicon single crystal substrate including an epitaxial layer (epitaxial wafer), a silicon single crystal ingot block, or an SOI wafer, other than the substrate W. Although FIGS. 1 and 4 show an example in which the light reflected at the surface of the substrate W is directly incident on the photodiode 4, the reflected light may be collected by a light collecting portion such as a lens, and be guided to the photodiode 4.

DESCRIPTION OF THE REFERENCE CHARACTERS 1 detection device
2 stage (moving portion)
2a r stage
2b θ stage
3 irradiator (irradiation portion)
3a semiconductor laser
3b mirror portion
4 photodiode (light-detecting portion)

5 evaluation portion (calculation portion, detection portion)
W substrate
S1 inclined surface
S2 flat surface
P1 first position
P2 second position
O axis

The invention claimed is:

1. A detection device comprising:
an irradiation portion that emits laser light to a surface of an object;
a light-detecting portion on which light resulting from the laser light reflected at the surface is incident, and that detects a first position at which the light is incident;
a calculation portion that calculates an inclination of the surface on the basis of the first position and a second position at which light is incident on the light-detecting portion when the laser light is reflected at the surface that is flat; and
a detection portion that detects a defect formed on the surface on the basis of the inclination calculated by the calculation portion.

2. The detection device according to claim 1, wherein the calculation portion calculates the inclination in a first direction extending in a horizontal direction on the basis of a difference between the first position and the second position in the first direction.

3. The detection device according to claim 2, wherein the calculation portion calculates the inclination in a second direction that is orthogonal to the first direction in the horizontal direction on the basis of a difference between the first position and the second position in the second direction.

4. The detection device according to claim 1, comprising a moving portion including a support portion that supports the object, and being movable in a horizontal direction and rotatable about an axis extending in a vertical direction, wherein
the surface is scanned with the laser light by the moving portion supporting and moving the object, and
the calculation portion calculates an inclination of the surface at each point on the basis of the first position of light resulting from the laser light reflected at the point on the surface.

5. The detection device according to claim 1, wherein
the surface of the object comprises a silicon single crystal,
the irradiation portion emits the laser light having a wavelength of 405 nm or less to the surface, and
the detection portion detects a slip dislocation that is the defect.

6. The detection device according to claim 1, wherein the light-detecting portion is a quadrant photodiode.

7. The detection device according to claim 1, wherein the object is a silicon single crystal substrate, a silicon single crystal substrate including an epitaxial layer, a silicon single crystal ingot block, or an SOI wafer.

8. A detection method comprising the steps of:
emitting laser light to a surface of an object;
calculating an inclination of the surface on the basis of a first angle that is a reflection angle of light resulting from the laser light reflected at the surface, and a second angle that is a reflection angle of light when the laser light is reflected at the surface that is flat; and
detecting a defect formed on the surface on the basis of the inclination calculated in the calculating step.

9. The detection method according to claim 8, wherein,
in the calculating step, the inclination in a first direction extending in a horizontal direction is calculated on the basis of a difference between the first angle and the second angle in the first direction.

10. The detection method according to claim 9, wherein,
in the calculating step, the inclination in a second direction that is orthogonal to the first direction in the horizontal direction is calculated on the basis of a difference between the first angle and the second angle in the second direction.

11. The detection method according to claim 8, wherein
the emitting step includes scanning the surface with the laser light by moving the object, and,
in the calculating step, an inclination of the surface at each point is calculated on the basis of the first angle of light resulting from the laser light reflected at the point on the surface.

12. The detection method according to claim 8, wherein,
in the emitting step, the laser light having a wavelength of 405 nm or less is emitted to the surface of the object, the surface of which comprises a silicon single crystal, and,
in the defect detecting step, a slip dislocation that is the defect is detected.

13. The detection method according to claim 8, wherein
a silicon single crystal substrate, a silicon single crystal substrate including an epitaxial layer, a silicon single crystal ingot block, or an SOI wafer is used as the object.

* * * * *